(12) United States Patent
Modi et al.

(10) Patent No.: US 9,517,084 B2
(45) Date of Patent: Dec. 13, 2016

(54) LEVEL DETECTION OF FOLLICLE FLUID IN A TEST TUBE

(71) Applicant: Shivani Scientific Industries Private Limited, Mumbai (IN)

(72) Inventors: Ashish Modi, Mumbai (IN); Ravikant Kale, Mumbai (IN)

(73) Assignee: SHIVANI SCIENTIFIC INDUSTRIES PRIVATE LIMITED, Mumbai (IN)

(*) Notice: Subject to any disclaimer, the term of this patent is extended or adjusted under 35 U.S.C. 154(b) by 161 days.

(21) Appl. No.: 14/601,861

(22) Filed: Jan. 21, 2015

(65) Prior Publication Data
US 2015/0201965 A1    Jul. 23, 2015

(30) Foreign Application Priority Data
Jan. 23, 2014    (IN) .......................... 243/MUM/2014

(51) Int. Cl.
*A61B 17/435* (2006.01)
*G01F 23/292* (2006.01)

(52) U.S. Cl.
CPC ......... *A61B 17/435* (2013.01); *G01F 23/2921* (2013.01); *G01F 23/2927* (2013.01)

(58) Field of Classification Search
CPC . A61B 17/435; G01F 23/2921; G01F 23/2927
USPC .............................. 250/577; 600/33; 340/620
See application file for complete search history.

(56) References Cited

U.S. PATENT DOCUMENTS

| 4,644,789 A | * | 2/1987 | Snyder | ................ G01F 23/2967 |
| | | | | 310/319 |
| 8,736,455 B2 | | 5/2014 | Linsenmeyer et al. | |
| 2014/0038283 A1 | * | 2/2014 | Jose | ....................... C12M 47/02 |
| | | | | 435/325 |

FOREIGN PATENT DOCUMENTS

| EP | 0185285 A2 | 6/1986 |
| EP | 2063236 A1 | 5/2009 |

OTHER PUBLICATIONS

Xin Liu, "Optical Systems to Evaluate Volume of Medial Samples in Opaque Test Tubes", A Dissertation Submitted by the Faculty of the University of Utah, Department of Mechanical Engineering, Aug. 2011; 124 pages.

* cited by examiner

*Primary Examiner* — Seung C Sohn
(74) *Attorney, Agent, or Firm* — Ditthavong & Steiner, P.C.

(57) ABSTRACT

The present disclosure discloses an apparatus and a method for detecting level of the follicle fluid falling into a test tube during an aspiration process. The apparatus may be configured for detecting the level of the follicle fluid falling into the test tube. Upon detecting that the level reaches the pre-defined threshold level in the test tube, the apparatus may be further configured to notify a doctor about the level of the follicle fluid into the test tube via an audio alarm or visually through the ultrasound monitor. The notification enables the doctor to concentrate on the aspiration process and further facilitates to prevent spilling of the follicle fluid from the test tube, once the follicle fluid reaches the pre-defined threshold level of the test tube.

8 Claims, 4 Drawing Sheets

LEVEL DETECTION OF FOLLICLE FLUID IN A TEST TUBE

PRIORITY INFORMATION

The present application claims priority to Indian Provisional Patent Application No. 243/MUM/2014, filed on Jan. 23, 2014, the entirety of which is hereby incorporated by reference.

TECHNICAL FIELD

The present disclosure described herein, in general, relates to a method and apparatus for detection of level of follicle fluid falling into a test tube.

BACKGROUND

In medical science, one of a treatment for infertility is 'IVF' (In Vitro Fertilization, universally known as the Test Tube Baby). As a part of procedure of the treatment, it is required that an oocyte (egg) is recovered from a female patient in an operation theatre with the female patient under anesthesia. The oocyte comprises the egg that can be fertilized outside the female patient body in order to produce a zygote. The zygote may then be transferred to another female patient's body to facilitate successful pregnancy.

In the present day situation, a doctor who is performing the oocyte recovery procedure has his/her both hands occupied in holding the ultrasound probe and the attached needle. He/she may be constantly observing an ultrasound monitor to assist him/her and guide the needle tip in order to reach the correct spot in the ovary where the oocyte can be reached and aspirated. It may be understood that an ultrasound oocyte recovery procedure is performed for extracting the oocyte from the ovaries within the female patient. In the aforesaid procedure, a vaginal ultrasound probe with an attached needle guide is passed into vagina of the female patient under sterile conditions and the needle is then passed through the top of the vagina into the ovary. The follicles are then aspirated until the oocyte is obtained. In order to obtain the oocyte through aspiration, an apparatus known as 'aspiration pump' or 'aspirator' may be utilized for generating a sufficient amount of vacuum that enables the extraction of the follicle fluid containing the oocyte from the female patient's body.

In order to start the aspiration procedure, a foot switch coupled with the aspiration pump is pressed. Upon pressing the foot switch, the follicle fluid along with the oocyte flows inside the needle. At certain stage of the oocyte recovery procedure, it may be observed that the outflow of the follicle fluid may collapse the follicle and at this point the foot switch has to be released to neutralize the vacuum on the needle tip. Therefore, a constant monitoring of the follicle fluid falling in the test tube required. Specifically, it is required to ensure that level of the follicle fluid doesn't exceed a pre-defined threshold level of the test tube, so that the follicle fluid does not spill out of the test tube which may cause damage to follicles present in the follicle fluid.

In a present day situation, a constant watch on the level of the follicle fluid falling into the test tube is maintained by a nurse assisting the doctor. The nurse may orally communicate with the doctor, constantly, regarding status of the level of the follicle fluid falling into the test tube. Since the status of the follicle fluid is relayed by the nurse, this may result in delay in communication. It is required that the doctor gets uninterrupted and accurate information on the status of the level of the follicle fluid so that the doctor's vision is dedicated to screen of the ultrasound monitor at the time of the operation.

SUMMARY

Before the present methods, are described, it is to be understood that this application is not limited to the particular methods, and methodologies described, as there can be multiple possible embodiments which are not expressly illustrated in the present disclosures. It is also to be understood that the terminology used in the description is for the purpose of describing the particular versions or embodiments only, and is not intended to limit the scope of the present application. This summary is provided to introduce concepts related to detecting level of follicle fluid falling into a test tube and the concepts are further described below in the detailed description. This summary is not intended to identify essential features of the disclosure nor is it intended for use in determining or limiting the scope of the disclosure.

According to various aspects of present disclosure, an apparatus and a method for detecting level of follicle fluid in a test tube is disclosed. The purpose of the apparatus is to detect the level of the follicle fluid falling into the test tube during recovering the oocytes from a female patient's body using an aspirator pump. Although the purpose and functioning of the apparatus described herein is by taking the follicle fluid as an example, but the apparatus may also be used for any other fluid or human body fluids that is to be extracted in the test tube.

In one embodiment, the apparatus and the method disclosed, is used to detect the level of the follicle fluid having transparent and/or opaque characteristics. In order to detect the level, the apparatus comprises a test tube, a casing, the aspirator pump, and a signal processing circuitry. The test tube is used to store follicle fluid. The casing, coupled with the test tube, comprises a first optical device and a second optical device. The first optical device and the second optical device may be positioned, on the test tube, in a manner such that the second optical device is aligned opposite to the first optical device. It may be understood that the first optical device emits beam of a pre-defined intensity, through the test tube, towards the second optical device. The aspirator pump, coupled with the test tube, is used to extract the follicle fluid in the test tube by generating vacuum pressure. The signal processing circuitry, coupled with the casing, facilitates to detect the level of the follicle fluid by monitoring intensity of the beam received by the second optical device. Upon receiving the intensity of the beam, the intensity may be compared with the pre-defined intensity. Subsequently, the level of the follicle fluid may be detected in the test tube when difference between the pre-defined intensity and the intensity is greater than a pre-defined threshold value. In one aspect, the difference is based on opacity or transparency properties of the follicle fluid. The level may indicate that the follicle fluid extracted in the test tube is reached to a pre-defined level.

In one aspect, upon detecting the level of the fluid at the pre-defined level, an alert mechanism may generate an alert for indicating an operator that the follicle fluid extracted in the test tube is reached to the pre-defined level. In one aspect, the alert generated may be an audio alert or a visual alert.

BRIEF DESCRIPTION OF THE DRAWINGS

The foregoing detailed description of embodiments is better understood when read in conjunction with the appended drawing. For the purpose of illustrating the disclosure, there is shown in the present document example constructions of the disclosure; however, the disclosure is not limited to the specific methods disclosed in the document and the drawings.

The detailed description is described with reference to the accompanying figure. In the figure, the left-most digit(s) of a reference number identifies the figure in which the reference number first appears. The same numbers are used throughout the drawings to refer like features and components.

The figure depicts an embodiment of the present disclosure for purposes of illustration only. One skilled in the art will readily recognize from the following discussion that alternative embodiments of the structures and methods illustrated herein may be employed without departing from the principles of the disclosure described herein.

DETAILED DESCRIPTION

Some embodiments of this disclosure, illustrating all its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items. It must also be noted that, the singular forms "a," "an," and "the" include plural references unless the context clearly dictates otherwise. Although any methods similar or equivalent to those described herein can be used in the practice or testing of embodiments of the present disclosure, the exemplary, methods are now described. The disclosed embodiments are merely exemplary of the disclosure, which may be embodied in various forms.

Various modifications to the embodiment will be readily apparent to those skilled in the art and the generic principles herein may be applied to other embodiments. However, one of ordinary skill in the art will readily recognize that the present disclosure is not intended to be limited to the embodiments illustrated, but is to be accorded the widest scope consistent with the principles and features described herein.

In one implementation, an apparatus for detecting level of follicle fluid containing oocyte extracted from a female patient's body in a test tube using an aspirator pump is disclosed. According to embodiments of present disclosure, while extracting the follicle fluid, the apparatus may be configured to detect whether the level of the follicle fluid in the test tube reaches a pre-defined level. In order to detect the level of the follicle fluid, the test tube may be coupled within a casing that enables electronic and optical components to work in unison for providing feedback to a doctor about the level of the follicle fluid extracted into the test tube, in real time.

In one aspect, the electronic and optical components may include, but not limited to an array of photo emitters and an array of photo detectors. As soon as the level of the follicle fluid reaches the pre-defined level, an alert signal may be generated. In one aspect, the alert signal may be an audio alarm or a visual indicator that notifies the doctor that the follicle fluid falling into the test tube has reached the pre-defined level. The detail working of the apparatus is further explained in detail in subsequent paragraphs.

General Working Conditions and Setup

Figure 1:
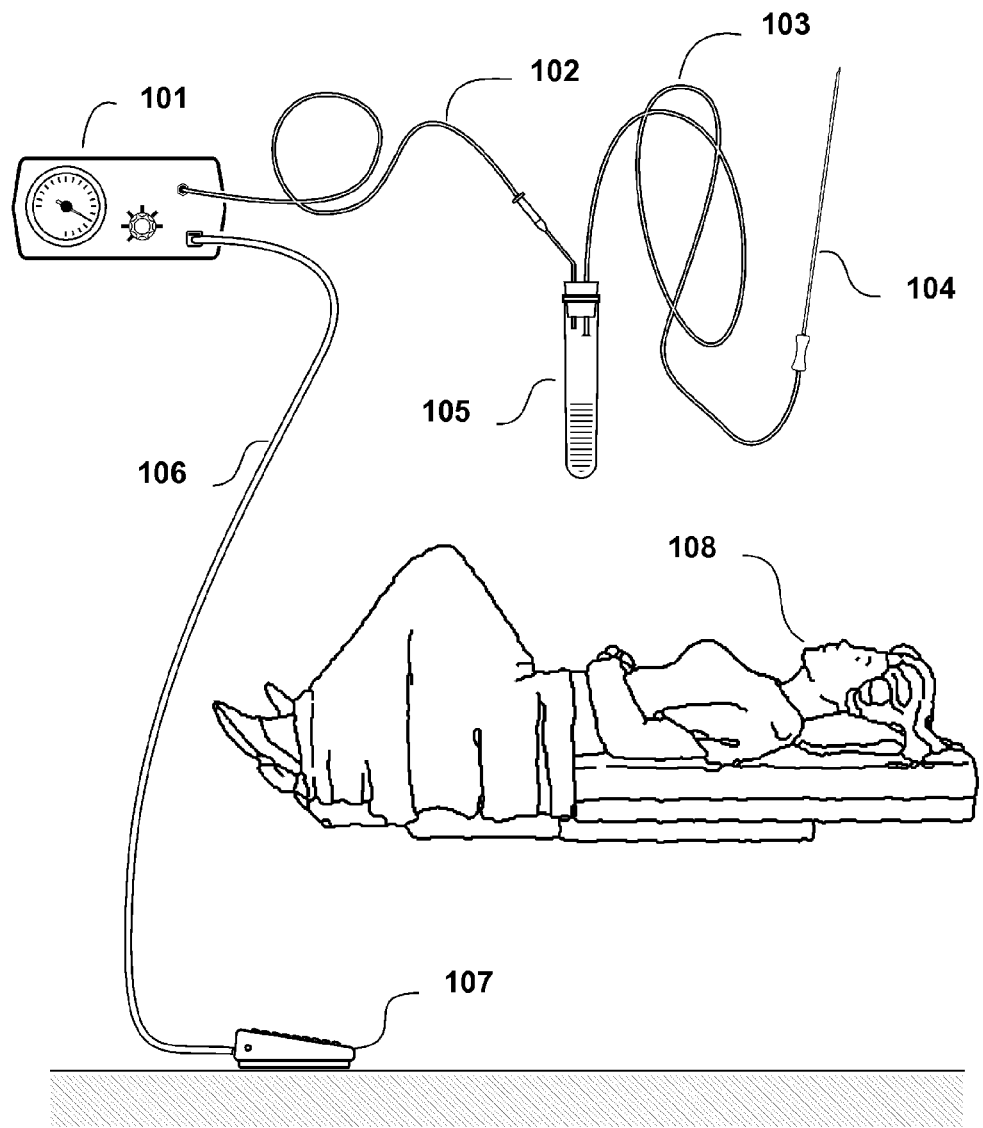
FIG. 1 is an Oocyte aspiration setup illustrating various components used in aspiration process for obtaining one or more oocyte from a female patient, in accordance with an embodiment of the present disclosure.

Referring to FIG. 1, an oocyte aspiration setup is shown, in accordance with an embodiment of present disclosure. The oocyte aspiration setup for retrieving an oocyte from a female patient is shown in detail. It may be seen from FIG. 1 that the female patient 108 is on an Operation Theatre (OT) table in a lithotomic position under anesthesia. Further, for performing the oocyte aspiration, various components are provided, wherein the components may comprise a vacuum generator apparatus 101, a suction tube 102, an inlet tube 103, a needle 104, a test tube 105, a cord 106 for connecting a foot switch 107 with the vacuum generator apparatus 101.

The vacuum generator apparatus 101, hereinafter referred to as an aspirator pump, is a main power operated device. The aspirator pump 101 is connected to the test tube 105 by the suction tube 102. The aspirator pump 101 may be also connected to the foot switch 107, which is placed on the floor for the doctor to operate whenever he/she requires vacuum to be generated in the suction tube 102 which is further connected to the test tube 105.

The other tube i.e., the inlet tube 103 coming out from the test tube 105 is attached to the long needle 104. Further, the needle 104 may be used to insert into the female patient's body till its tip reaches her ovaries, where the oocyte are found suspended in the follicle fluid.

In general practice, the test tube 105 is held in the hand by a nurse or any other person assisting the doctor during the aspiration. The nurse is supposed to give a feedback to the doctor orally about status of the level of the follicle fluid falling into the test tube 105. Thus, during this oral communication there may be a chance of a mismatch or misunderstanding between the nurse and the doctor. Hence, in order to overcome such situation the apparatus, for automatically detecting the level of the follicle fluid falling into the test tube 105 and thereby notifying the doctor by means of an audio alarm or a visual indicator that the level of the follicle fluid has reached the pre-defined level in the test tube 105, is described below.

Apparatus 200

Figure 2:
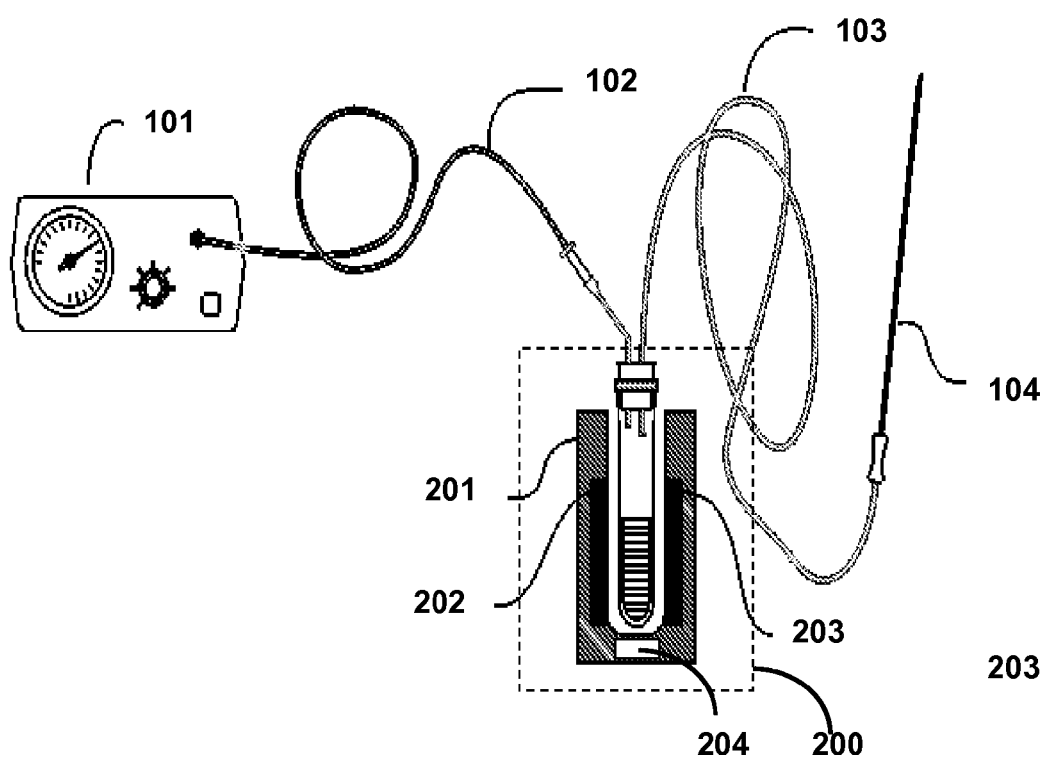
FIG. 2 illustrates an arrangement of an apparatus comprising a test tube in which the follicle fluid is to be collected.

Referring to FIG. 2, an apparatus 200 and a test tube 105 in which the follicle fluid is to be collected shown, in accordance with an embodiment of present disclosure. The apparatus may comprise a casing 201 in order to hold the test tube 105 in its designed cavity appropriately made to measure for the test tube 105. The test tube 105 is placed in the designed cavity in such a manner that it gets aligned with optical devices. The optical devices may comprise a first optical device 202 and a second optical device 203. In one embodiment, the first optical device 202 and the second optical device 203 may be responsible for detecting the level of the follicle fluid falling into the test tube 105. In one aspect, the first optical device 202 and the second optical device 203 and a signal processing circuitry 204 may reside inside the apparatus 200.

Location of Optical Devices

Figure 3:
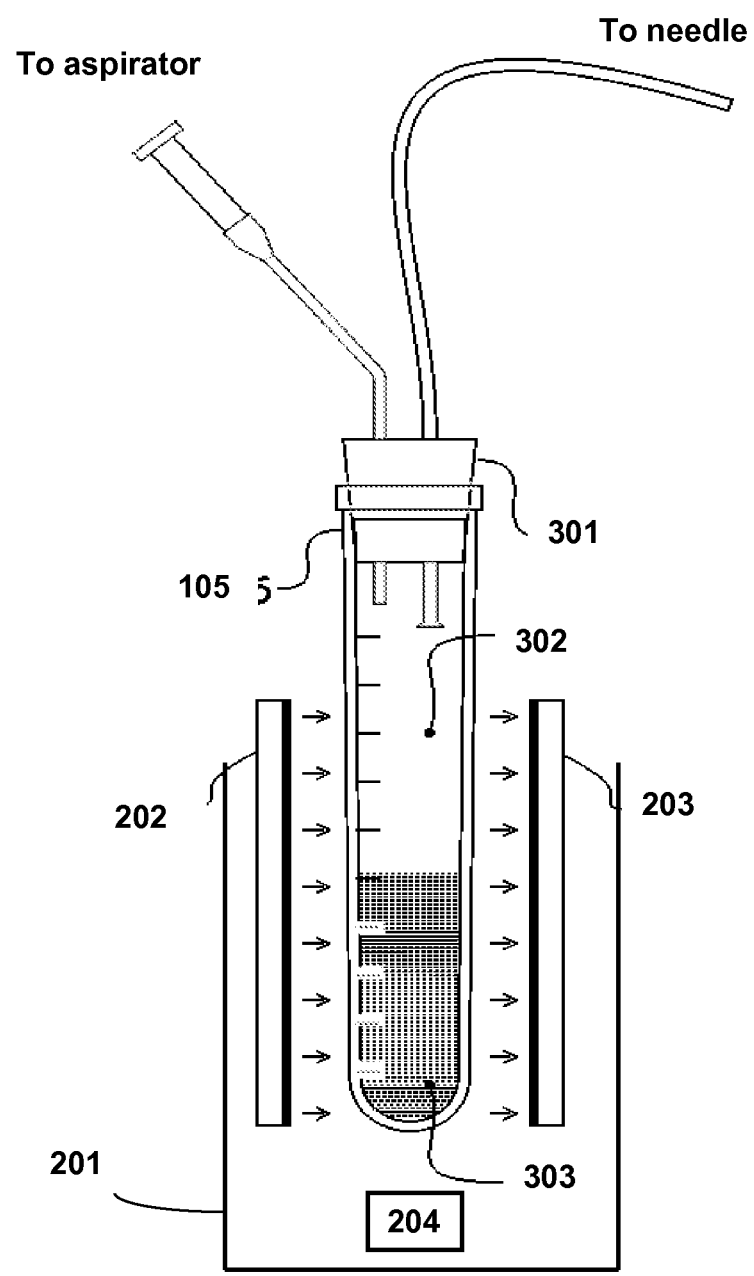
FIG. 3 illustrates an arrangement of casing comprising optical devices and other components of the apparatus.

Referring to FIG. 3, illustrates an arrangement of casing 201 comprising optical devices of the apparatus 200 along with the test tube 105, in accordance with an embodiment of present disclosure. As aforementioned, the optical devices may further comprise the first optical device 202 and the second optical device 203. In one embodiment, the first optical device 202 may be an array of infra-red (IR) light emitting diodes (LEDs) and the second optical device 203 may be an array of infra-red (IR) detectors. As shown in the FIG. 3, the first optical device 202 and the second optical device 203 may be positioned, on the test tube 105, in a manner such that the second optical device 203 is aligned opposite to the first optical device 202.

In one example, the test tube 105 may be coupled to the array of infra-red (IR) light emitting diodes, wherein each LED may be configured to emit a light beam through the test tube 105. It may be understood that from the FIG. 3 that the test tube 105 may be divided into multiple sub-levels, wherein corresponding to each sub-level, an LED is deployed. Similarly, the test tube 105 may further be coupled to the array of IR detectors, wherein each IR detector is deployed corresponding to each LED of the test tube 105. Further, each IR detector may be configured to detect light beam emitted by the LED corresponding to the IR detector in order to detect whether the pre-defined threshold level of the follicle fluid in the test tube 105 has reached. In one aspect, the pre-defined threshold level has reached or nor is determined by a signal processing circuitry 204 coupled with the casing 201. The signal processing circuitry 204 ensures the detection of the level of the fluid in the test tube 105. The functioning of the signal processing circuitry 204 is described in detail by referring the apparatus 200 illustrated in FIG. 4 as below.

Detail Functioning of the Apparatus 200

Figure 4A:
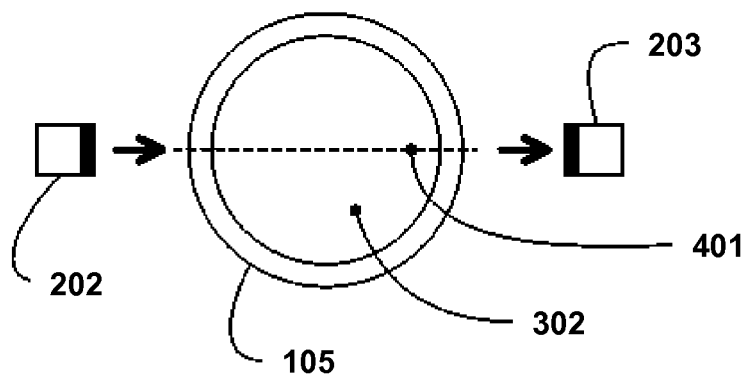
FIGS. 4(a) and 4(b) illustrates a functional block diagram of the apparatus, in accordance with one embodiment of the present disclosure.
Figure 4B:
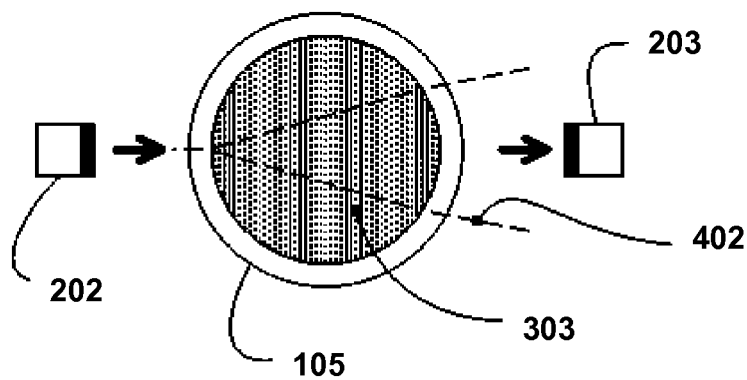

Referring to FIGS. 4(a) and 4(b), a functional block diagram of the apparatus 200 is illustrated, in accordance with an embodiment of present disclosure. It may be understood that, the level detection of the follicle fluid is carried out by the optical devices, wherein the optical devices comprises a first optical device 202 and a second optical device 203 aligned, opposite to the first optical device 202, on the test tube 105. In addition to the optics involved for detecting the level, a signal processing circuitry 204, coupled with the casing 201, further ensures the detection of the level of the fluid in the test tube 105. In one aspect, the first optical device 202, as aforementioned, may be the array of infra-red (IR) light emitting diodes (LEDs). Each infra-red LED may be deployed at a specific level in the test tube 105 for detecting the level of the follicle fluid in the test tube 105. For example, the array of infra-red (IR) LEDs may comprise a $LED_1$, a $LED_2$, a $LED_3$, and a $LED_4$ deployed at sub-levels of $5_{ml}$, $10_{ml}$, $15_{ml}$, and $20_{ml}$ respectively of the test tube 105. It may be understood that, the light beam 401 emitted by the $LED_1$, the $LED_2$, the $LED_3$, and the $LED_4$ may be detected by the array of IR detectors $D_1$, $D_2$, $D_3$ and $D_4$ aligned on the opposite side of the $LED_1$, the $LED_2$, the $LED_3$, and the $LED_4$ respectively on the test tube 105. In one aspect, the $D_1$, the $D_2$, the $D_3$ and the $D_4$ may be coupled with the test tube 105 corresponding to the $LED_1$, the $LED_2$, the $LED_3$, and the $LED_4$ respectively.

In order to detect the level, the signal processing circuitry 204, initially, monitors intensity of the beam received by the second optical device 203. After monitoring the intensity, the signal processing circuitry compares the intensity of the beam with a pre-defined intensity. In one aspect, the pre-defined intensity indicates the intensity of light emitted by the first optical device 202. Subsequently, the signal processing circuitry 204 detects the level of the follicle fluid in the test tube 105 when difference between the pre-defined intensity and the intensity is greater than a pre-defined threshold value. In one aspect, the level may indicate that the follicle fluid extracted in the test tube 105 may reach at a pre-defined level. In order to understand the functioning of the signal processing circuitry 204, consider an example where the pre-defined intensity is 100 units, the intensity received, by the second optical device, is 80 units, and the pre-defined threshold value is 15. Now in order to detect the level, the signal processing circuitry 204 calculates the difference between the pre-defined intensity and the intensity (i.e. 100-80).

Upon calculating, it may be understood that the difference is 100-80 units=20 units. Since the predefined threshold value set for the difference is 15 units (i.e. beam to be received by the second optical device 203 should not deviate by more than 15 units), therefore in this case the level is detected by the signal processing circuitry 204.

In one embodiment, the level of the follicle fluid may be detected by using the opacity property of the follicle fluid having opaque characteristics. In another embodiment, the level of the follicle fluid may be detected by using the refractive property of the follicle fluid having transparent characteristics.

In one example, in order to understand the working of the array of LEDs and the array of detectors in unison for the detection of the level of follicle fluid, consider the combination of the $LED_1$ and the $D_1$. As can be understood from the FIG. 4(a), the $LED_1$ present in the first optical device 202 may constantly emit light beam 401 that may be detected by the $D_1$ located on the opposite side of $LED_1$. It may be understood that $D_1$ detects the light beam 201 when there is no obstruction in the test tube 105 by any external means. This ensures that the follicle fluid has not reached the pre-defined level (i.e. $5_{ml}$) marked in the test tube 105.

However, during the recovery procedure, when the follicle fluid is collected into the test tube 105, at a certain instance, the light beam 401 emitted by the first optical device 202 may be obstructed or refracted by the follicle fluid and hence does not allow the second optical device 203 to detect the light beam 401. It may be understood that the follicle fluid collected into the test tube 105 may have the opaque or the transparent characteristics. In one embodiment, when the follicle fluid is having the opaque characteristics, then there will be obstruction created by the follicle fluid (e.g. assuming the follicle present in the follicle fluid is dark in color) for the passage of the light beam 401 emitted by the $LED_1$ to the $D_1$. This in turn, enables the second optical device 203 to ensure that the follicle fluid has reached the pre-defined level for example, 5 ml in this case.

In another embodiment, when the follicle fluid is having the transparent characteristics, then there will be no obstruction created by the follicle fluid. Since the follicle fluid is having transparent characteristics, the light beam 401 emitted by the $LED_1$ may pass through the follicle fluid and thereby causing refraction of the light beam 401 due to the presence of the follicle fluid in the test tube 105. Since, the light beam 401 is refracted, the $D_1$ corresponding to the $LED_1$ may not be able to detect the light beam 401. This in turn, enables the detector 201 to ensure that the follicle fluid has reached the pre-defined level.

Similarly, using the combinations of other LEDs and the corresponding IR detectors, the apparatus 200 may be enabled to ensure that the follicle fluid has reached the multiple sub-levels (e.g. $10_{ml}$, and $15_{ml}$) of the test tube 105. In one aspect, the apparatus 201, via the signal processing circuitry 204, may further facilitate the doctor to view on the ultrasound monitor, the gradual filling of the test tube 105 with the follicle fluid, as-and-when the follicle fluid reaches the multiple sub-levels, and finally the pre-defined threshold level is reached.

Once the follicle fluid reaches the pre-defined level, an alert mechanism enables the doctor to stop the extraction and/or retrieval of oocytes from the female patient's body and thereby conclude the collection of the follicle fluid in the test tube 105. In one aspect, the alert may be generated as an audio alert or a visual alert. In one aspect, the audio indicator may be an audio signal such as buzzer. The alert mechanism facilitates to prevent spilling of the follicle fluid from the test tube 105 during the extraction of the oocyte from the female patient's body, once the pre-defined level is reached.

Although implementations for methods for detecting level of follicle fluid have been described in language specific to structural features and/or methods, it is to be understood that the implementations and/or embodiments are not necessarily limited to the specific features or methods described.

Exemplary embodiments discussed above may provide certain advantages. Though not required to practice aspects of the disclosure, these advantages may include those provided by the following features The present disclosure enables to prevent spilling of the follicle fluid from the test tube during the extraction of the oocyte from the patient's body.

The present disclosure enables to detect the level of the follicle fluid of varied optical characteristics like the opaque and transparent characteristics.

We claim:

1. A method for detecting level of follicle fluid in a test tube, the method comprising:
   positioning a first optical device and a second optical device, on a test tube, in a manner such that the second optical device is aligned opposite to the first optical device, wherein the first optical device emits beam of a pre-defined intensity, through the test tube, towards the second optical device;
   extracting follicle fluid in the test tube by generating vacuum pressure using an aspirator;
   monitoring, via a signal processing circuitry, intensity of the beam received by the second optical device;
   comparing, via a signal processing circuitry, the intensity of the beam with the pre-defined intensity; and
   detecting, via a signal processing circuitry, the level of the follicle fluid in the test tube when difference between the pre-defined intensity and the intensity is greater than a pre-defined threshold value, wherein the level indicates that the follicle fluid extracted in the test tube is reached to a pre-defined level.

2. The method of claim 1 further generates an alert for indicating an operator that the follicle fluid extracted in the test tube is reached to the pre-defined level.

3. The method of claim 1, wherein the alert is generated as an audio alert or a visual alert.

4. The method of claim 1, wherein the difference is based on the opacity or transparency properties of the follicle fluid.

5. An apparatus for detecting level of follicle fluid in a test tube, the apparatus comprising:
   a test tube for storing follicle fluid;
   a casing coupled with the test tube, wherein the casing comprises a first optical device and a second optical device, and wherein the first optical device and the second optical device are positioned, on the test tube, in a manner such that the second optical device is aligned opposite to the first optical device, and wherein the first optical device emits beam of a pre-defined intensity, through the test tube, towards the second optical device; and
   a signal processing circuitry, coupled with the casing, facilitates to detect the level of the follicle fluid by
      monitoring intensity of the beam received by the second optical device,
      comparing the intensity of the beam with the pre-defined intensity, and
      detecting the level of the follicle fluid in the test tube when difference between the pre-defined intensity and the intensity is greater than a pre-defined threshold value, wherein the level indicates that the follicle fluid extracted in the test tube is reached to a pre-defined level.

6. The apparatus of claim 5 further an alert mechanism for generating an alert for indicating an operator that the follicle fluid extracted in the test tube is reached to the pre-defined level.

7. The apparatus of claim 5, wherein the alert is generated as an audio alert or a visual alert.

8. The apparatus of claim 5, wherein the difference is based on opacity or transparency properties of the follicle fluid.

* * * * *